(12) United States Patent
Al Bisher

(10) Patent No.: US 11,160,959 B2
(45) Date of Patent: Nov. 2, 2021

(54) FLEXIBLE-TIP-CATHETER (BISHER CATHETER)

(71) Applicant: Imam Abdulrahman Bin Faisal University, Dammam (SA)

(72) Inventor: Hassan Mohammed A. Al Bisher, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 131 days.

(21) Appl. No.: 16/661,430

(22) Filed: Oct. 23, 2019

(65) Prior Publication Data
US 2021/0121669 A1   Apr. 29, 2021

(51) Int. Cl.
*A61M 27/00* (2006.01)
*A61M 25/00* (2006.01)
*A61M 25/01* (2006.01)

(52) U.S. Cl.
CPC ........ *A61M 27/00* (2013.01); *A61M 25/0054* (2013.01); *A61M 25/0147* (2013.01); *A61M 2025/0161* (2013.01)

(58) Field of Classification Search
CPC .............. A61M 27/00; A61M 25/0021; A61M 25/0054; A61M 25/0147; A61M 2025/0161; A61M 25/0662; A61M 1/008; A61M 2025/0163; A61M 2210/101
See application file for complete search history.

(56) References Cited

U.S. PATENT DOCUMENTS

| | | | |
|---|---|---|---|
| 4,033,331 A | 7/1977 | Guss et al. | |
| 4,586,923 A * | 5/1986 | Gould ............. | A61M 25/09033 600/434 |
| 5,472,435 A * | 12/1995 | Sutton ................. | A61M 25/005 604/540 |
| 6,126,649 A * | 10/2000 | VanTassel ......... | A61M 25/0138 604/528 |
| 6,887,229 B1 * | 5/2005 | Kurth ................. | A61M 25/0041 604/525 |
| 8,241,246 B2 | 8/2012 | Dzakula et al. | |
| 2009/0043299 A1 * | 2/2009 | Racz ................. | A61M 25/0147 606/41 |

FOREIGN PATENT DOCUMENTS

CN        203971148 U    12/2014

* cited by examiner

*Primary Examiner* — Nicholas J Weiss
*Assistant Examiner* — Eric Rassavong
(74) *Attorney, Agent, or Firm* — Oblon, McClelland, Maier & Neustadt, L.L.P.

(57) ABSTRACT

A catheter having a head with a head orifice and a head channel connected to the head orifice, a primary lumen wall that defines an internal primary lumen volume, an adjustable neck that connects the head channel to the internal primary lumen volume, an adjustment system partially enclosed in the primary lumen wall that provides an articulation of the adjustable neck between an extended position to a contracted positon, wherein the articulation from the extended position to the contracted position provides a flexible tip catheter while the articulation from the contracted position to the extended position provides an ability to angulate toward a target.

13 Claims, 15 Drawing Sheets

FLEXIBLE-TIP-CATHETER (BISHER CATHETER)

BACKGROUND

In today's medicine, catheters are widely used for a broad range of functions. For example, catheters can be used to treat diseases and/or perform surgical procedures relating to cardiovascular, urological, gastrointestinal, neurovascular, and hepatobiliary applications.

Mechanical properties are crucial components of catheters as the mechanical properties and notably the stiffness and/or the ability to bend directly impact the maneuverability of the catheters and the chance to successfully treat diseases and/or perform surgical procedures.

For some instances when maneuverability is important, e.g. to follow torturous paths present in veins and/or to avoid vital body organs, a flexible tip catheter is preferred whereas when an application of flexibility is important, e.g. to perforate tissues or cannulate structure, a flexible tip catheter is preferred.

To this end, conventional catheters are manufactured with different materials and/or sizes to provide different stiffness levels. Although such conventional catheters are widely used, they present important drawbacks. Notably, in such conventional catheters the stiffness level and/or the bending cannot be modified while a catheter is in use, thus requiring the use of a plurality of conventional catheters during a single disease treatment and/or surgical procedure.

Thus, a catheter solving the aforementioned problem of providing a bending that can be adjusted while in use is desired.

SUMMARY

Accordingly, the object of the present disclosure is to provide a catheter which overcomes the above-mentioned limitations.

The catheter of the present disclosure allows for the adjustment of the bending via a neck supporting a penetrating head that can be articulated to increase and decrease an angular orientation of the neck.

In one non-limiting illustrative example, a catheter is presented. The catheter includes a head with a head orifice and a head channel connected to the head orifice, a main lumen wall that defines an internal main lumen volume, may also contains lateral orifices especially for drainage e.g. chest cavity or abscess cavity, an adjustable neck that connects the head channel to the internal main lumen volume, the adjustable neck having an anterior neck ring affixed to the head, a posterior neck ring affixed to the main lumen wall, and a tensioner that generates a bias force between the anterior neck ring and the posterior neck ring, and an adjustment system having a secondary lumen with an internal portion that is enclosed along the main lumen wall, and an external portion that protrudes from the main lumen wall, a filament that runs through the internal portion and the external portion, the filament having an anterior filament end that is affixed to the anterior neck ring, and a posterior filament end that exits from the external part, and an adjuster that pulls and releases the posterior filament end to provide a decrease and an increase of an inter neck ring distance between the anterior neck ring and the posterior neck ring, wherein the decrease of the inter neck ring distance increases the bias force and provides an angular orientation increase of the catheter while the increase of the inter neck ring distance decreases the bias force and provides an angular orientation decrease of the catheter.

In another non-limiting illustrative example, a catheter is presented. The catheter includes a head with head orifice and a head channel connected to the head orifice, a main lumen wall that defines an internal main lumen volume, an adjustable neck that connects the head channel to the internal main lumen volume, the adjustable neck having an anterior neck ring affixed to the head a posterior neck ring affixed to the main lumen wall and a tensioner that generates a bias force between the anterior neck ring and the posterior neck ring, an adjustment system partially enclosed in the main lumen wall that provides a decrease and an increase of an inter neck ring distance between the anterior neck ring and the posterior neck ring, wherein the decrease of the inter neck ring distance increases the bias force and provides an angular orientation increase of the catheter while the increase of the inter neck ring distance decreases the bias force and provides an angular orientation decrease of the catheter. In addition, the catheter may contain lateral orifices connected to the main lumen useful for the drainage of cavity filled with fluid or air e.g. chest cavity or abscess.

In another non-limiting illustrative example, a catheter is presented. The catheter includes a head with a head orifice and a head channel connected to the head orifice, a main lumen wall that defines an internal main lumen volume, an adjustable neck that connects the head channel to the internal main lumen volume, an adjustment system partially enclosed in the main lumen wall that provides an articulation of the adjustable neck between an extended position to a contracted positon, wherein the articulation from the extended position to the contracted position provides an angular orientation increase of the catheter while the articulation from the contracted position to the extended position provides an angular orientation decrease of the catheter.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1A:
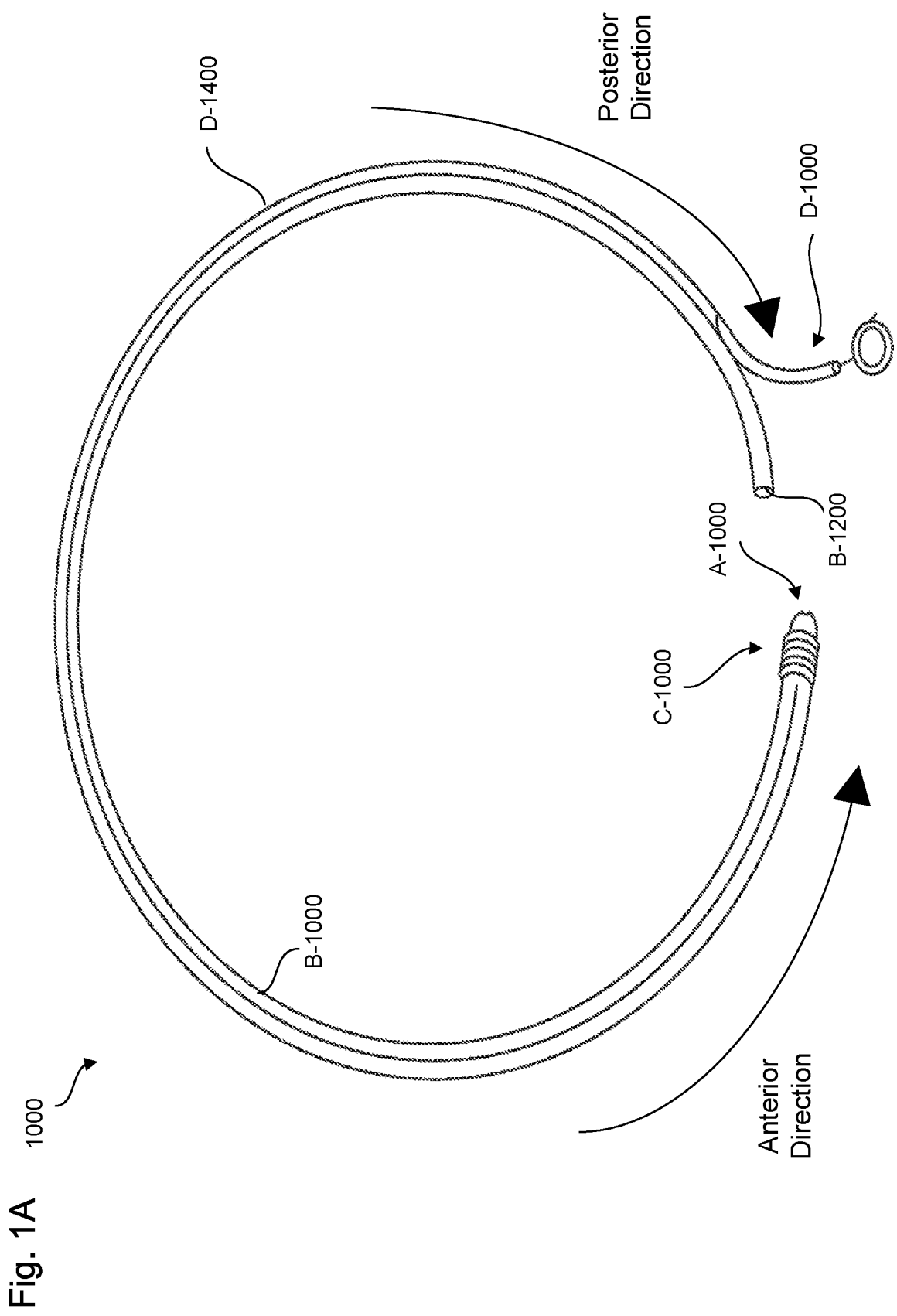
FIG. 1A is a complete perspective view of a catheter in an extended position, according to certain aspects of the disclosure.

All publications, patent applications, patents, and other references mentioned herein are incorporated by reference in their entirety. Further, the materials, methods, and examples discussed herein are illustrative only and are not intended to be limiting.

In the drawings, like reference numerals designate identical or corresponding parts throughout the several views. Further, as used herein, the words "a", "an", and the like include a meaning of "one or more", unless stated otherwise. The drawings are generally drawn not to scale unless specified otherwise or illustrating schematic structures or flowcharts.

Figure 1B:
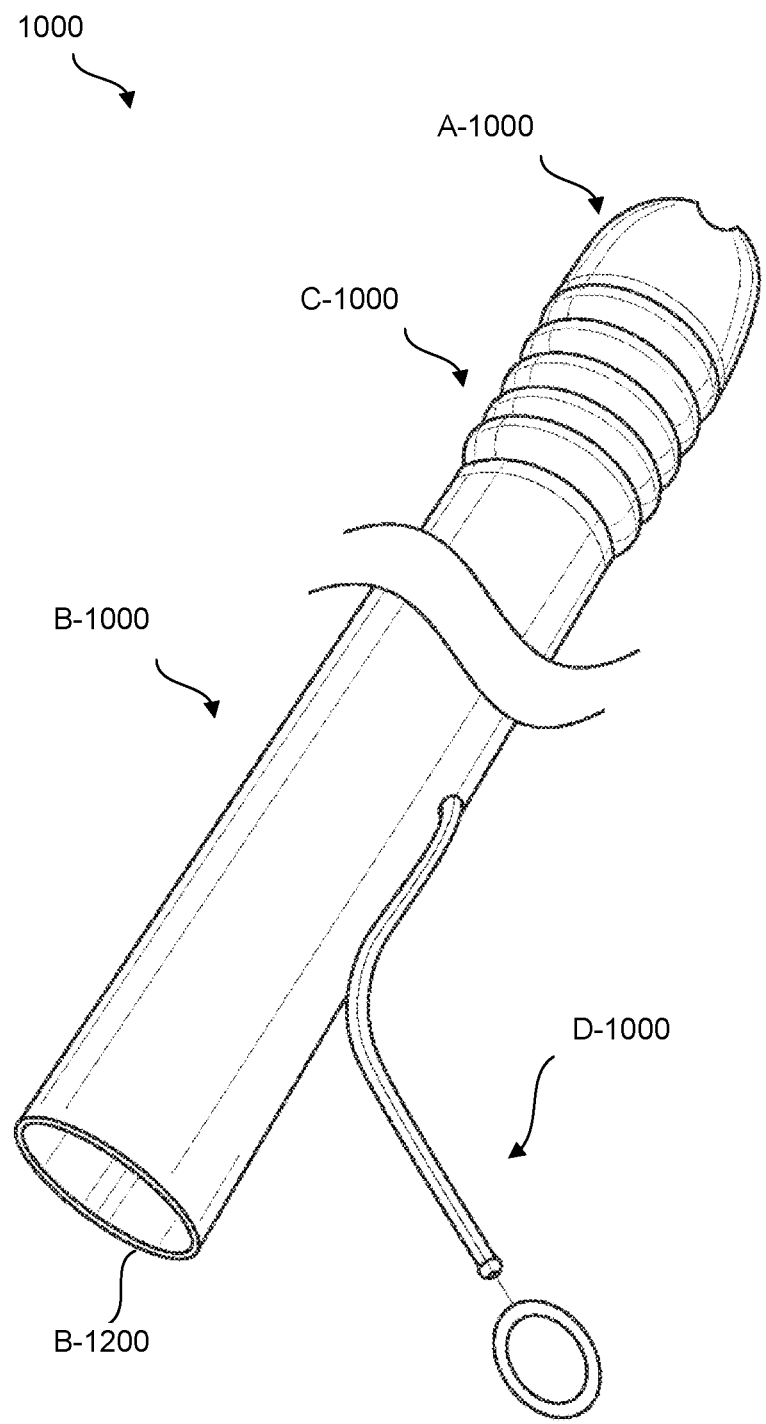
FIG. 1B is a partial perspective view of the catheter in an extended position, according to certain aspects of the disclosure.
Figure 1C:
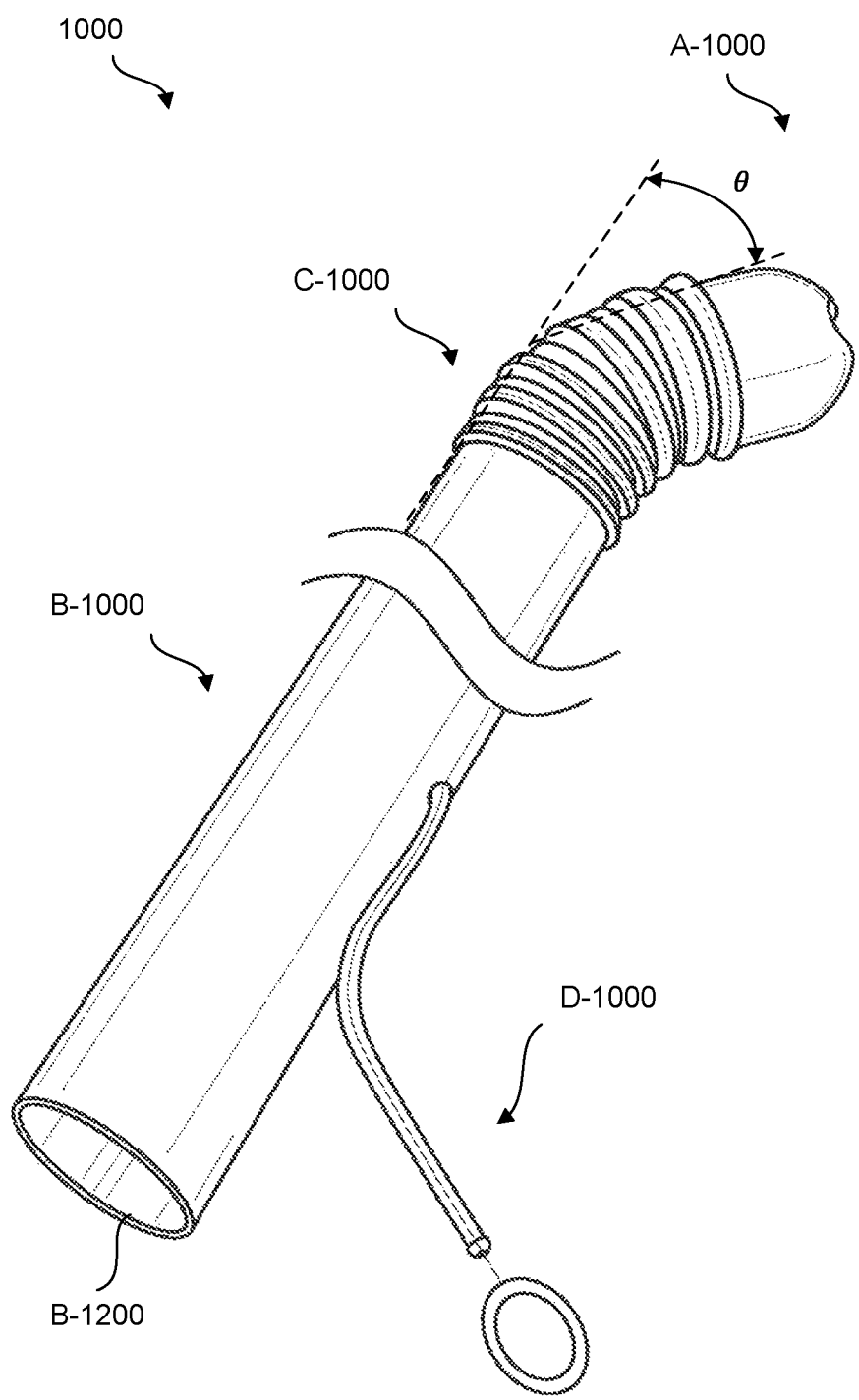
FIG. 1C is a perspective view of the catheter in an contracted position, according to certain aspects of the disclosure.

FIGS. 1A-1C are a complete perspective view of a catheter 1000 and partial perspective views of an adjustable neck C-1000 of the catheter in an extended position and contracted position, respectively and according to certain aspects of the disclosure.

The catheter 1000 can include a main lumen B-1000, a head A-1000, an adjustable neck C-1000 that connects the main lumen B-1000 and the head A-1000, and an adjustment system D-1000 that extends along the adjustable neck C-1000 and along a partition of the main lumen B-1000.

Under the action of the operator, the catheter 1000 can be inserted into a body from an entrance location, e.g. a perforation performed by the head A-1000 and/or a body orifice, and travel inside the body up to a target location, e.g. organ to be treated, with a posterior lumen extremity B-1200 of the catheter 1000 being placed outside the body. Once the head A-1000 has reached the target location, the main lumen B-1000 can channel fluids, e.g. urine, blood, and air, and/or solid objects, e.g. coils, and wires, from the posterior lumen extremity B-1200 to the target location, and vice versa.

As used herein, the term "posterior" refers to the region of the catheter 1000 closest to the posterior lumen extremity B-1200, and the term "anterior" refers to the region of the catheter 1000 closest to the head A-1000, as illustrated by arrows in FIG. 1A.

The catheter 1000 through the adjustable neck C-1000 and the adjustment system D-1000 provides an angular orientation θ for the catheter 1000 that can be adjusted, e.g. increased and decreased, by the operator. The adjustment of the angular orientation θ can extend the range of functions, applications, and/or facilitate operations for which the catheter 1000 is employed. By increasing and/or decreasing the angular orientation θ, the catheter 1000 can be employed in applications dealing with different body parts, tissues, and/or organs having different physical characteristics, e.g. density, softness, elasticity, such as cardiovascular, urological, gastrointestinal, neurovascular, and ophthalmic applications.

For example, decreasing the angular orientation θ of the catheter 1000 and particularly the angular orientation θ of the adjustable neck C-1000 that supports the head A-1000 can facilitate insertion through hard tissues and/or organs e.g. skin, muscles, protective membranes, by the head A-1000, while increasing the angular orientation θ can facilitate the guidance of the head A-1000 through obstacles and delicate parts, e.g. strong curvatures present in cavities, soft tissues, and/or membranes.

In addition, through the adjustment system D-1000 the operator can adjust the angular orientation θ of the catheter 1000 while the catheter 1000 is in use, e.g. the catheter 1000 is traveling from the entrance location to the target location, and vice-versa.

Figure 2:
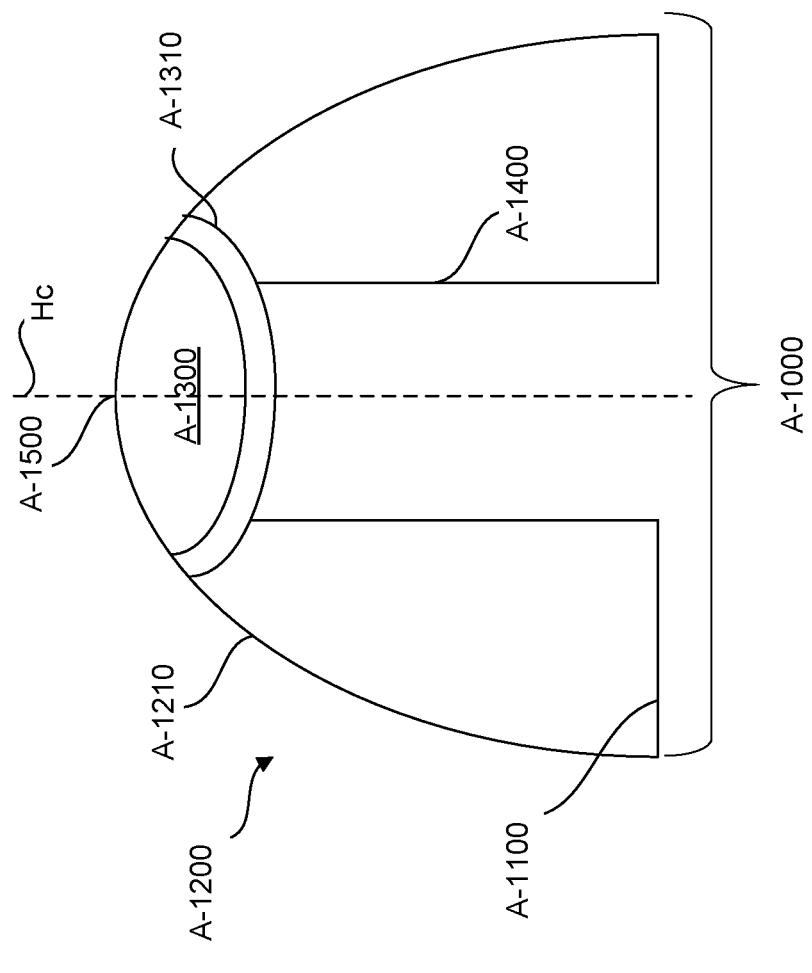
FIG. 2 is sectional view of a head of the catheter, according to certain aspects of the disclosure.

FIG. 2 is sectional view of the head A-1000 of the catheter 1000, according to certain aspects of the disclosure.

The head A-1000 of the catheter 1000 can include a head base A-1100 affixed to an anterior extremity of the adjustable neck C-1000, a head tip A-1200 that sits on the head base A-1100, a head orifice A-1300 that is placed on an anterior portion of the head tip A-1200, a head channel A-1400 that connects the head orifice A-1300 to the adjustable neck C-1000, and an orifice edge A-1310 that delimits the head orifice A-1300.

The head base A-1100 can provide support to the head tip A-1200 and transmit substantially uniformly forces applied on the head tip A-1200 to the adjustable neck C-1000 when the catheter 1000 is inserted through the entrance location and travels along the path from the entrance location to the target location.

The head tip A-1200 can have a shape that facilitates the insertion of the head A-1000 through the entrance location and along the path from the entrance location to the target location. For example, the head tip A-1200 can have a semi-ellipsoidal shape, a central axis $H_c$ that is substantially centered along the head channel A-1400 and the catheter 1000, and a pole A-1500 that is substantially centered on the head orifice A-1300.

In addition, the head tip A-1200 can have a tip external surface A-1210 substantially smooth to facilitate the insertion of the head A-1000 through the entrance location and the travel of the head A-1000 along the path from the entrance location to the target location.

The head orifice A-1300 can be substantially aligned with the head channel A-1400 with the orifice edge A-1310 that punctures body elements, e.g. tissues and/or organs, when the catheter 1000 is inserted through the entrance location and/or reaches the target location.

The head A-1000 may be made of metallic alloys such as surgical stainless steel alloys, plastic alloys, and/or the same material has the lumen main lumen B-1000 of the catheter 1000 to provide a smooth finishing of the tip external surface A-1210 of the head tip A-1200 and a sharp finishing to the orifice edge A-1310 of the head orifice A-1300.

Figure 3:
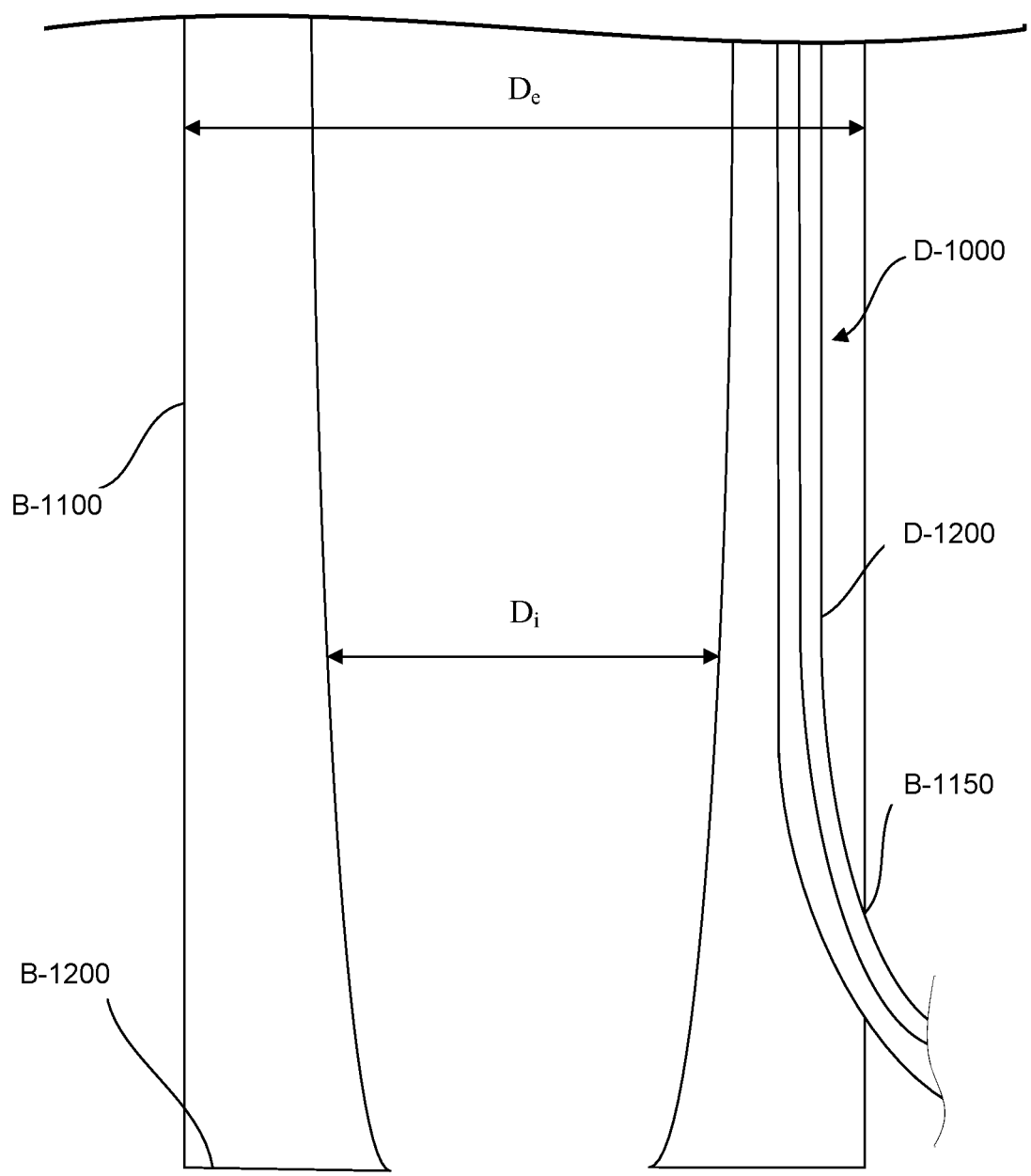
FIG. 3 is sectional view of the main lumen of the catheter, according to certain aspects of the disclosure.

FIG. 3 is sectional view of the main lumen B-1000 of the catheter 1000, according to certain aspects of the disclosure.

The main lumen B-1000 can have a tubular shape with an internal diameter $D_i$ and an external diameter $D_e$ that defines a main lumen wall B-1100.

The main lumen wall B-1100 can partially enclose the adjustment system D-1000 from an anterior lumen extremity B-1300 affixed to the adjustable neck C-1000 to a bifurcation portion B-1150 where a secondary lumen D-1200 of the adjustment system D-1000 protrudes from the main lumen B-1000. The partial enclosure of the adjustment system D-1000 provides an access to the adjustable neck C-1000 while leaving an external surface of the main lumen wall B-1100 substantially free of deformations, e.g. protrusions, bumps, or any variations in the external diameter $D_e$. The lack of deformations of the external surface of the main lumen wall B-1100 facilitates the insertion of the catheter 1000 through the entrance location and the travel of the catheter 1000 along the path from the entrance location to the target location.

The main lumen wall B-1100 can be made of flexible and translucent materials such as medical grade polymers, e.g. silicone rubber, nylon, polyurethane, polyethylene terephthalate (PET), latex, and/or thermoplastic elastomers, to enable the catheter 1000 to easily bend and follow curves that may be present along the path from the entrance location to the target location and to provide to the operator visibility of the fluids and/or the objects that are channeled through the main lumen B-1000.

In a non-limiting illustrative example, the main lumen B-1000 can have a flexibility that varies along a length of the main lumen B-1000. The flexibility can increase gradually from the posterior lumen extremity B-1200 to the anterior lumen extremity B-1300 of the main lumen B-1000 to provide maneuverability towards the posterior lumen extremity B-1200 and rigidity towards the head A-1000. For example, to gradually increase the flexibility from the posterior lumen extremity B-1200 to the anterior lumen extremity B-1300 the internal diameter $D_i$ of the main lumen B-1000 can increase gradually, e.g. linearly, polynomially, or exponentially, from the posterior lumen extremity B-1200 to the anterior lumen extremity B-1300 of the main lumen B-1000 while the external diameter $D_e$ of the main lumen B-1000 is maintained constant, as illustrated in FIG. 3.

Figure 4A:
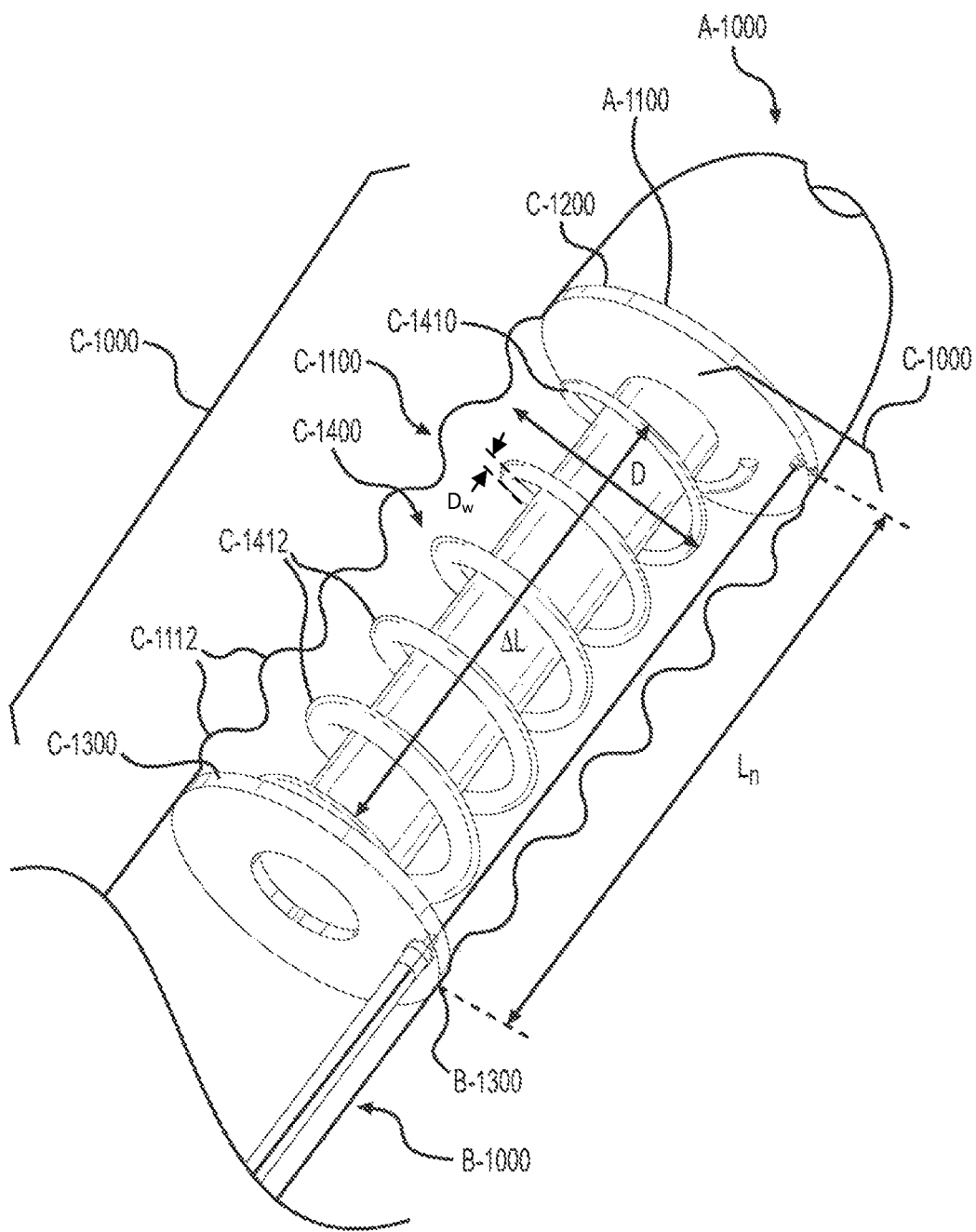
FIG. 4A is a perspective view of the adjustable neck of the catheter in the extended position, according to certain aspects of the disclosure.
Figure 4B:
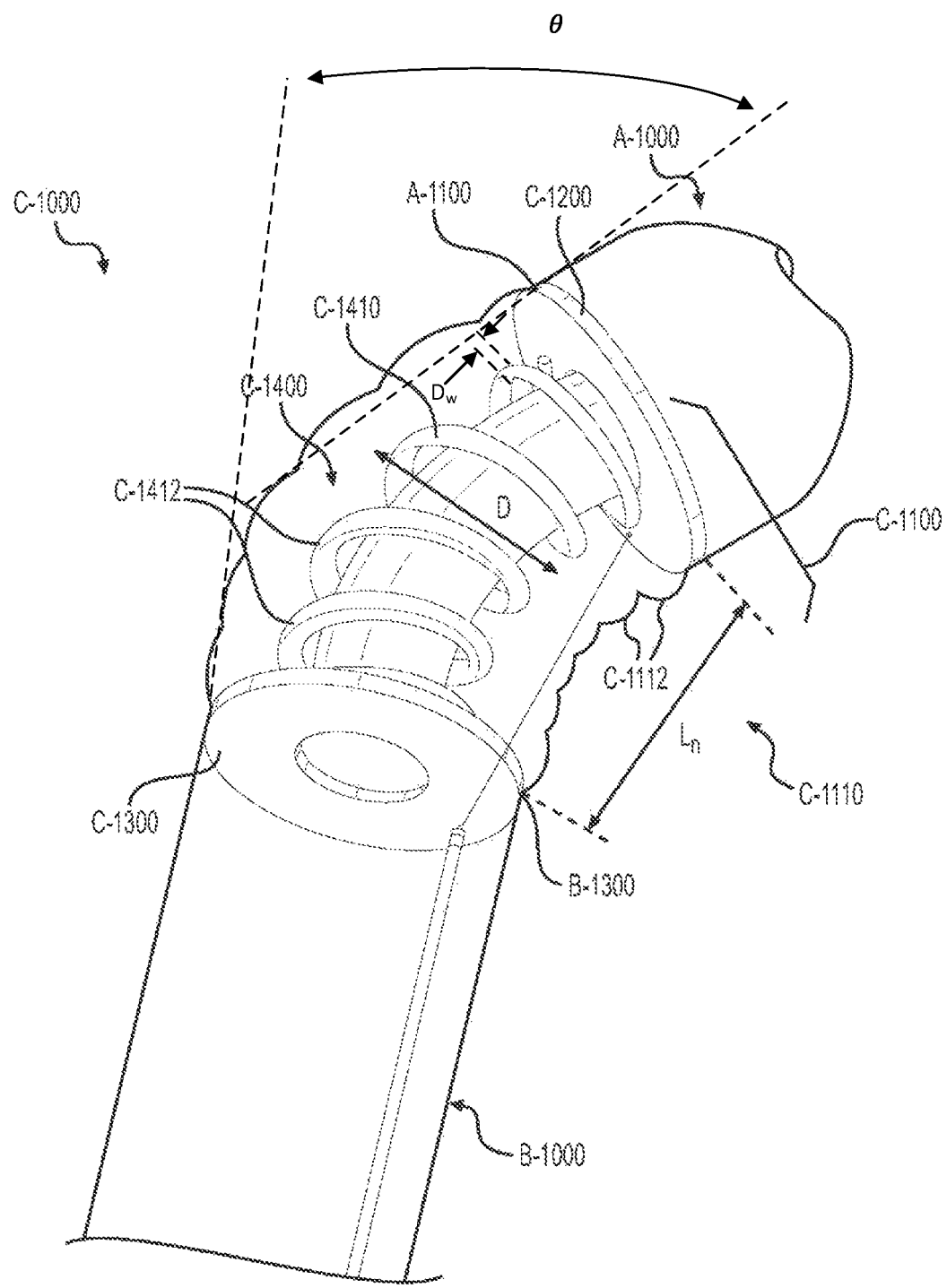
FIG. 4B is a perspective view of the adjustable neck in the contracted position, according to certain aspects of the disclosure.

FIGS. 4A-4B are perspective views of the adjustable neck C-1000 in the extended and contracted positions, respectively and according to certain aspects of the disclosure.

The adjustable neck C-1000 can include an anterior neck ring C-1200 affixed to the head base A-1100 of the head A-1000, a posterior neck ring C-1300 affixed to the anterior lumen extremity B-1300 of the main lumen B-1000, a neck tube C-1100 that extends from the anterior neck ring C-1200 to the posterior neck ring C-1300, a tensioner C-1400 that extends between the anterior neck ring C-1200 and the posterior neck ring C-1300 and that is enclosed inside an internal volume of the neck tube C-1100.

The tensioner C-1400 provides an adjustable bias force between the anterior neck ring C-1200 and the posterior neck ring C-1300 that can be increased when the adjustable neck C-1000 is articulated from the extended position to the contracted position and decreased when the adjustable neck C-1000 is articulated from the contracted position to the extended position. The anterior neck ring C-1200 transmits the adjustable bias force to the main lumen B-1000, the posterior neck ring C-1300 transmits the adjustable bias force to the head A-1000, and the neck tube C-1100 that encloses the tensioner C-1400 reacts to the adjustable bias force by providing an angular orientation θ commensurate with the adjustable bias force.

Through the adjustment system D-1000, the operator can move the posterior neck ring C-1300 closer to the anterior neck ring C-1200 and increase the adjustable bias force exerted by the tensioner C-1400 to provide an angular orientation increase. Reciprocally, through the adjustment system D-1000, the operator can move the posterior neck ring C-1300 away from the anterior neck ring C-1200 and decrease the adjustable bias force exerted by the tensioner C-1400 to provide an angular orientation decrease.

In a non-limiting illustrative example, the neck tube C-1100 can include an external neck wall C-1110 with structural elements that facilitates the articulation of the adjustable neck C-1000 from the extended position to the contracted position, and vice-versa. For example, the external neck wall C-1110 of the neck tube C-1100 can include a plurality of bulges C-1112 placed along a length of the neck tube C-1100 to facilitate the articulation of the adjustable neck C-1000 from the extended position to the contracted position and vice-versa.

The tensioner C-1400 can be at least one spring C-1410, e.g. coil spring, volute spring, helical spring, or the like, having physical characteristics, e.g. an tensioner elongation length ΔL, a tensioner diameter D, a tensioner number of coils N, such that the articulation of the catheter 1000 from the extended position to the contracted position can be performed by an average human strength without assistance of machinery or external source of power. For example, the tensioner elongation length ΔL can be between 0.01 millimeter and 100 millimeters and preferably between 1 millimeter and 10 millimeters, the tensioner diameter D can be between 0.3 millimeter and 10 millimeters and preferably between 1 millimeter and 5 millimeters, and the tensioner number of coils N can be between 1 and 100 and preferably between 1 and 10.

Figure 5:
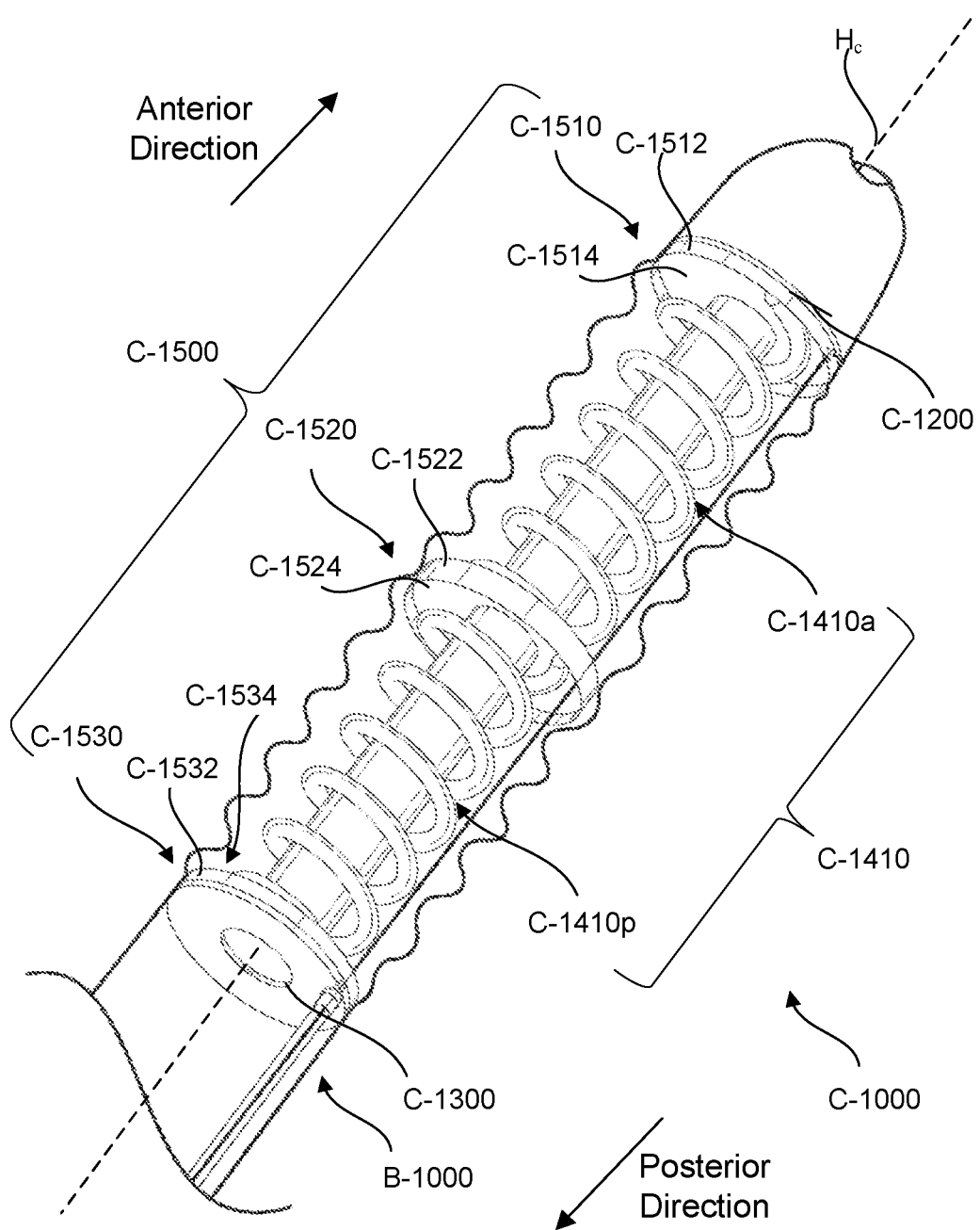
FIG. 5 is a perspective view of the adjustable neck with an anti-buckling system, according to certain aspects of the disclosure.

FIG. 5 is a perspective view of the adjustable neck C-1000 with an anti-buckling system C-1500, according to certain aspects of the disclosure.

The adjustable neck C-1000 can include an anti-buckling device C-1500 to prevent the adjustable neck C-1000 from bending, e.g. having the head A-1000 substantially misaligned with the main lumen B-1000, when the adjustable neck C-1000 is articulated from the extended position to the contracted position.

The anti-buckling system C-1500 can include a posterior seat C-1530 that provides support between the posterior neck ring C-1300 and a posterior spring C-1410p of the at least one spring C-1410, an anterior seat C-1510 that provides support between the anterior neck ring C-1200 and an anterior spring C-1410a of the at least one spring C-1410, and a separator C-1520 that separates the posterior spring C-1410p and the anterior spring C-1410a. The separator C-1520 may be moveably affixed along the central axis $H_c$ of the anterior spring C-1410a and the posterior spring C-1410p to prevent the at least one spring C-1410 from buckling when the at least one spring C-1410 is compressed due to the articulation of the adjustable neck C-1000 from the extended position to the contracted position.

The separator C-1520 may include a separator base portion C-1524 and a separator flange portion C-1522 that protrudes substantially perpendicularly from a peripheral edge of the separator base portion C-1524. The separator base portion C-1524 may be adapted to receive an posterior side of the anterior spring C-1410a and a anterior side of the posterior spring C-1410p. Further, the separator flange portion C-1522 may be adapted to receive and hold the anterior spring C-1410a and the posterior spring C-1410p.

Similarly to the separator C-1520, the anterior seat C-1510 may include an anterior seat base portion C-1514 and an anterior seat flange portion C-1512 that protrudes substantially perpendicularly from a peripheral edge of the anterior seat base portion C-1514. The anterior seat base portion C-1514 may be adapted to receive an anterior side of the anterior spring C-1410*a*. Further, the anterior seat flange portion C-1512 may be adapted to receive and hold the anterior spring C-1410*a*.

Similarly to the separator C-1520 and the anterior seat C-1510, the posterior seat C-1530 may include a posterior seat base portion C-1534 and a posterior seat flange portion C-1532 extending from a peripheral edge of the posterior seat base portion C-1534. The posterior seat base portion C-1534 may be adapted to receive a posterior side of the posterior spring C-1410*p*. Further, the posterior seat flange portion C-1532 may be adapted to receive and hold the posterior spring C-1410*p*.

Figure 6A:
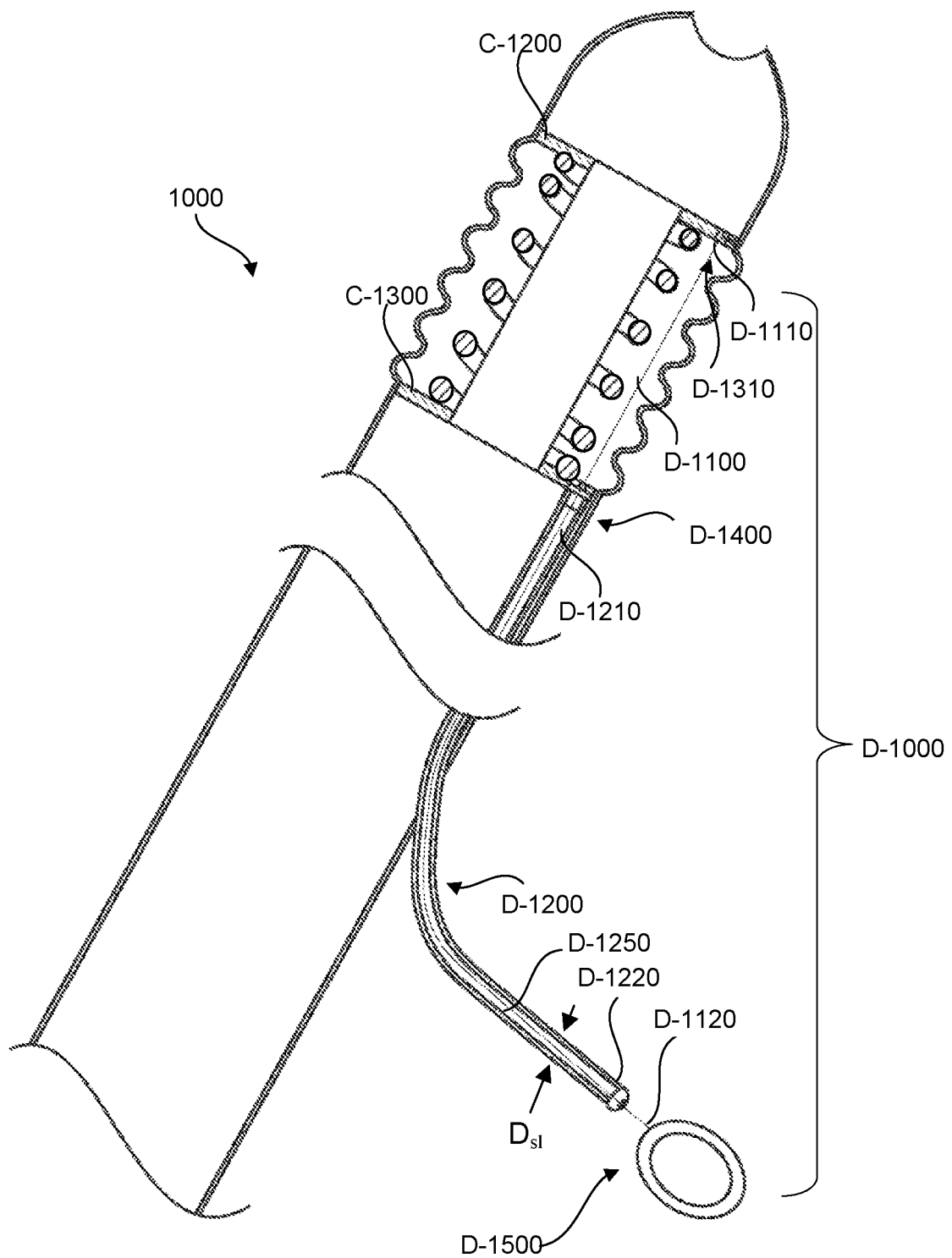
FIG. 6A is a sectional view of an adjustment system of the catheter in the extended position, according to certain aspects of the disclosure.
Figure 6B:
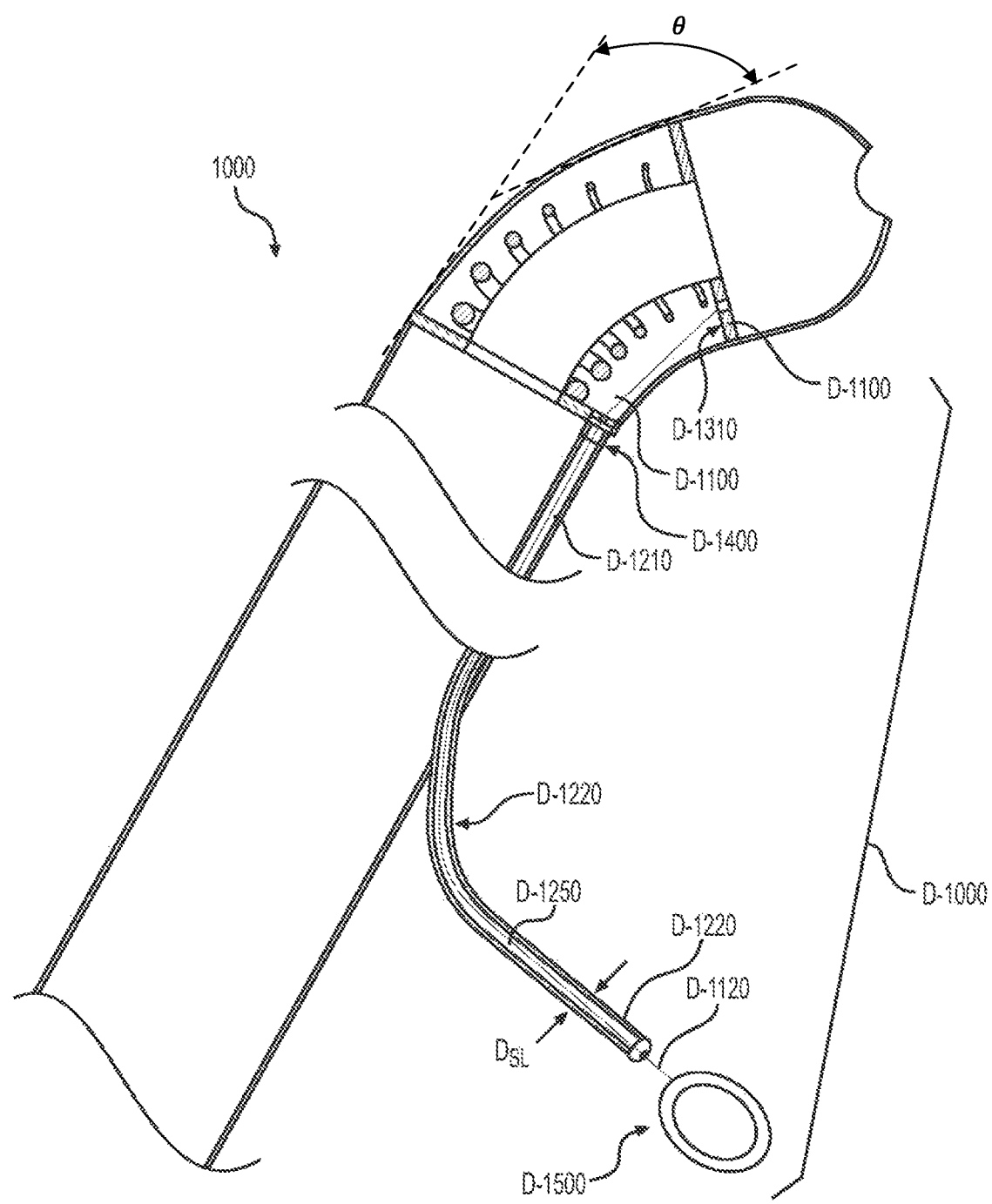
FIG. 6B is a sectional view of the adjustment system in the contracted position, according to certain aspects of the disclosure.

FIGS. 6A-6B are sectional views of the adjustment system D-1000 of the catheter 1000 in the extended position and in the contracted position, respectively and according to certain aspects of the disclosure.

The adjustment system D-1000 can include a secondary lumen stop D-1400 on the posterior neck ring C-1300, an anchor D-1310 on the anterior neck ring C-1200, the secondary lumen D-1200 having an internal extremity D-1210 that seats on the secondary lumen stop D-1400 and an external extremity D-1220 that is placed outside the main lumen B-1000, an adjuster D-1500 placed at the external extremity D-1220, a filament D-1100 that extends from the anchor D-1310 to the adjuster D-1500 and along an internal volume of the secondary lumen D-1200.

The anchor D-1310 affixes the filament D-1100 to the anterior neck ring C-1200, the secondary lumen stop D-1400 maintains the secondary lumen D-1200 affixed to the posterior neck ring C-1300 and the secondary lumen D-1200 acts as a sheath to allow the filament D-1100 to travel inside the secondary lumen D-1200 when the catheter 1000 is articulated between the extended and contracted positions through operation of the adjuster D-1500.

To increase the angular orientation θ of the catheter 1000, the operator articulates the catheter 1000 from the extended position to the contracted position through the adjuster D-1500. The adjuster D-1500 pulls the filament D-1100 in the posterior direction and the filament D-1100 pulls the anterior neck ring C-1200 towards the posterior neck ring C-1300 to reduce an inter neck ring distance $I_n$ between the anterior neck ring C-1200 and the posterior neck ring C-1300. When the inter neck ring distance $I_n$ is reduced, the tensioner C-1400 is compressed, distances between coils C-1412 of the at least one spring C-1410 are reduced and the angular orientation θ of the catheter 1000 is increased.

To decrease the angular orientation θ of the catheter 1000, the operator articulates the catheter 1000 from the contracted position to the extended position through the adjuster D-1500. The adjuster D-1500 releases the filament D-1100 in an inward direction and the filament D-1100 lets the anterior neck ring C-1200 move away from the posterior neck ring C-1300 to increase the inter neck ring distance $I_n$. When the inter neck ring distance is increased, the tensioner C-1400 is extended, distances between the coils C-1412 of the at least one spring C-1410 are increased and the angular orientation θ of the catheter 1000 is decreased.

The secondary lumen D-1200 can have a diameter $D_{sl}$ that is smaller than a thickness of the main lumen wall B-1100, e.g. a difference between the external diameter $D_e$ and the internal diameter $D_i$ at the posterior neck ring C-1300, to be enclosed in the main lumen wall B-1100 from the posterior neck ring C-1300 to the bifurcation portion B-1150.

In addition, the secondary lumen D-1200 may have an stiffness substantially higher than a stiffness of the main lumen B-1000 to prevent longitudinal compression of the secondary lumen D-1200 and withstand loads generated by the filament D-1100 on the secondary lumen D-1200 when the catheter 1000 is articulated from the extended position to the contracted position.

Alternatively, the secondary lumen D-1200 may have an internal surface coated with a liner D-1250 to reduce friction between the secondary lumen D-1200 and the filament D-1100 and facilitate the articulation of the catheter 1000 from the extended position to the contracted position, and vice-versa, For example, the liner D-1250 may be made from synthetic materials that provide wear-resistance and a slippery surface such as acetal homopolymer materials.

In addition, the liner D-1250 can be made of a radiopaque material to obstruct the passage of radiant energy, e.g. x-rays, and be visible in radiology imaging procedures.

The filament D-1100 may have physical characteristics, e.g. diameter and/or material composition, selected to avoid a breaking, tearing, and/or elongation from happening when the catheter 1000 is articulated. For example, the filament D-1100 may have a filament diameter $D_s$ between 0.001 millimeter and 0.100 millimeter, and preferably between 0.025 millimeter and 0.075 millimeter. The material composition of the filament D-1100 may be a metallic alloy such as a MP35N steel alloy.

In a non-limiting illustrative example, the adjustable neck C-1000 can have a flexibility that varies along the length $L_n$ of the adjustable neck C-1000. The flexibility can increase gradually from the anterior neck ring C-1200 to the posterior neck ring C-1300 of the adjustable neck C-1000 to facilitate the adjustment of the angular orientation θ of the adjustable neck C-10000. For example, to gradually increase the flexibility from the anterior neck ring C-1200 to posterior neck ring C-1300, a wire diameter $D_w$ of the tensioner C-1400 can increase gradually, e.g. linearly, polynomially, or exponentially, from the anterior neck ring C-1200 to the posterior neck ring C-1300, as illustrated in FIGS. 4A-4B and 6A-6B.

Figure 7:
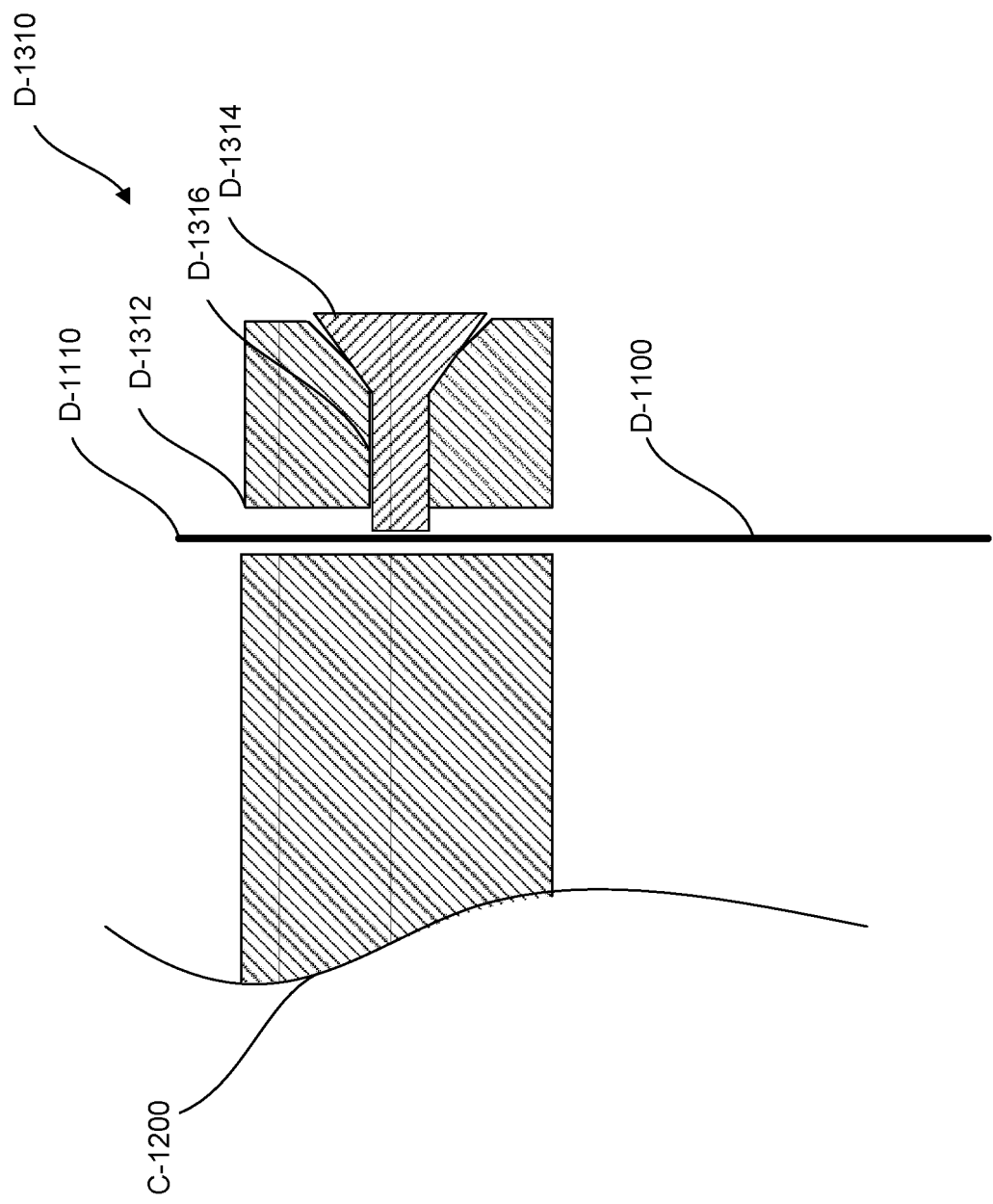
FIG. 7 is a sectional view of an anchor of the adjustment system, according to certain aspects of the disclosure.

FIG. 7 is a sectional view of the anchor D-1310 of the adjustment system D-1000, according to certain aspects of the disclosure.

The anchor D-1310 can include a filament hole D-1312 to receive an anterior filament extremity D-1110 of the filament D-1100, a filament screw D-1314, and a threaded hole D-1316 intersecting and opening on the filament hole D-1312 to receive the filament screw D-1314. The filament D-1100 is affixed to the anterior neck ring C-1200 by inserting the anterior filament extremity D-1110 of the filament D-1100 in the filament hole D-1312 and screwing the filament screw D-1314 in the threaded hole D-1316 and onto the anterior filament extremity D-1110. Also, the filament extremity d-1110 may affixed to the anterior neck ring c-1200 through looping around the neck ring c-1200 or through welding.

Figure 8:
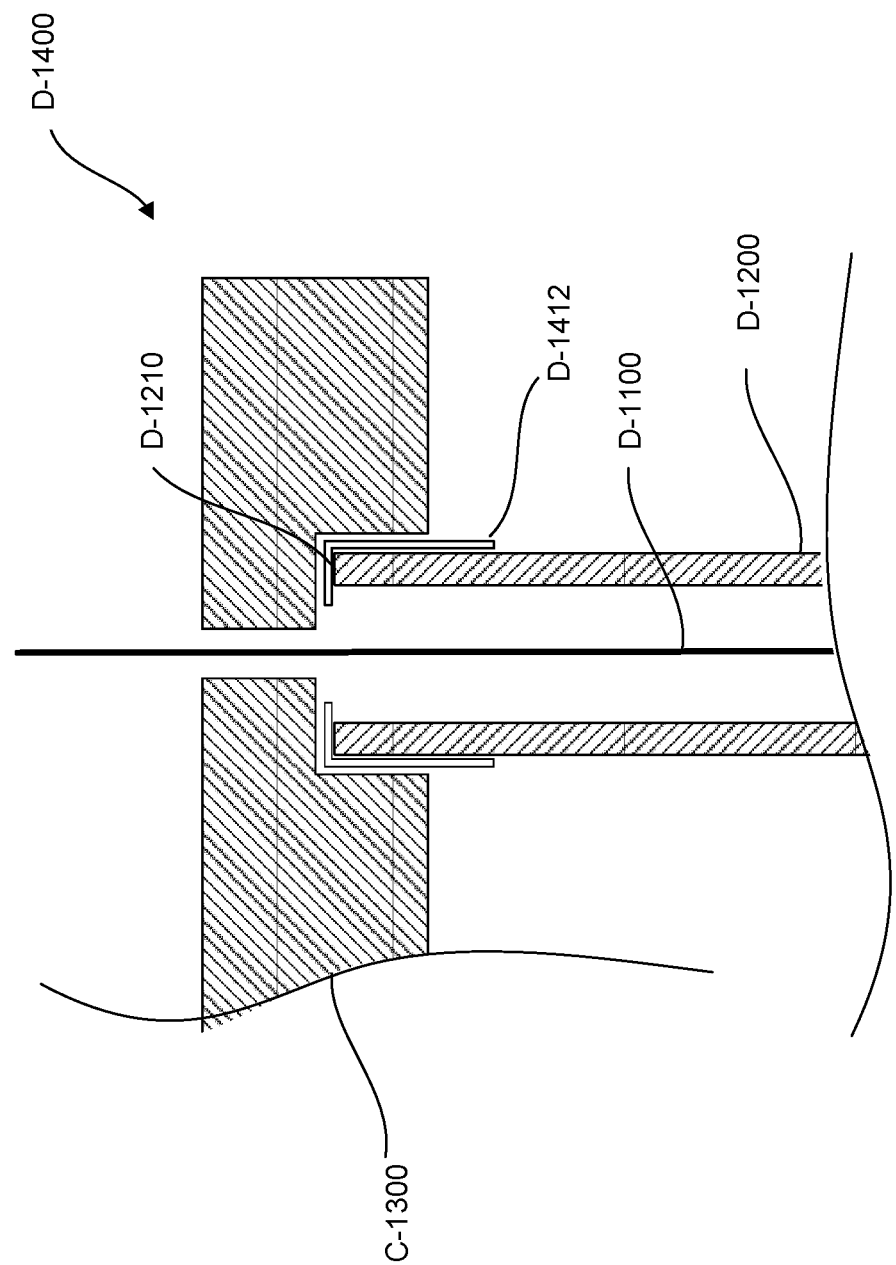
FIG. 8 is sectional view of a secondary lumen stop of the adjustment system, according to certain aspects of the disclosure.

FIG. 8 is sectional view of the secondary lumen stop D-1400 of the adjustment system D-1000, according to certain aspects of the disclosure.

The secondary lumen stop D-1400 can be counter bore hole with a large hole to receive the internal extremity D-1210 of the secondary lumen D-1200 and a small through hole to block the internal extremity D-1210 of the secondary lumen D-1200 and let the filament D-1100 pass freely through the posterior neck ring C-1300. In addition, a ferrule D-1412 may be inserted around the internal extremity D-1210 of the secondary lumen D-1200 to provide better attachment of the secondary lumen D-1200 inside the secondary lumen stop D-1400.

Figure 9A:
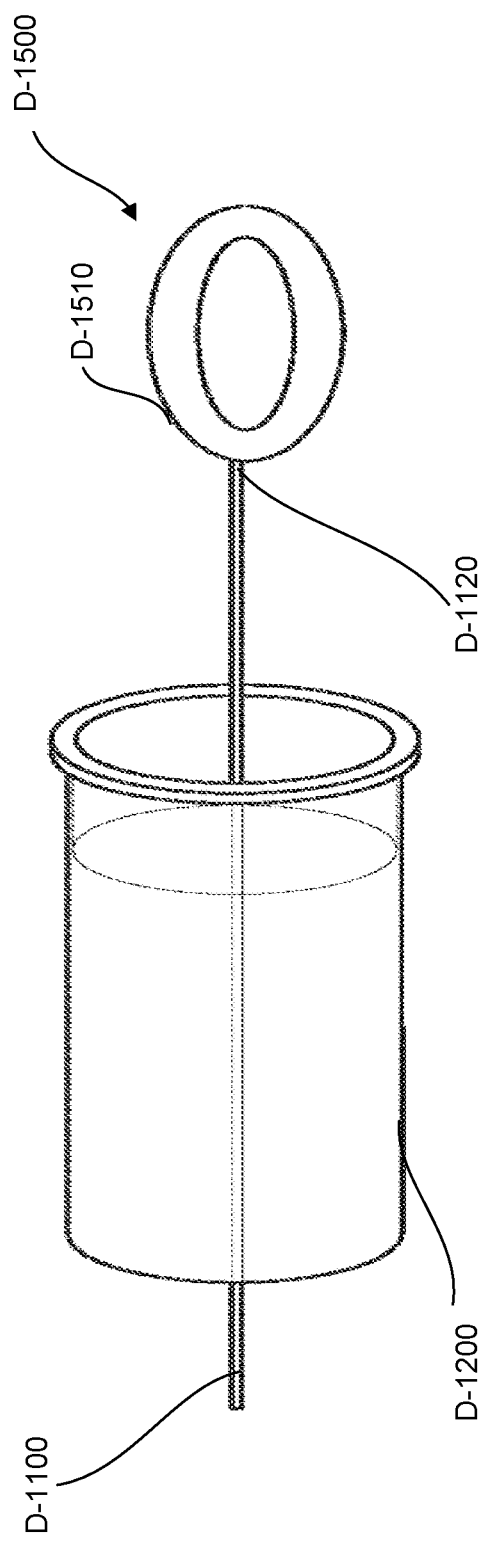
FIG. 9A is a perspective view of an adjuster of the adjustment system in a first configuration, according to certain aspects of the disclosure.
Figure 9B:
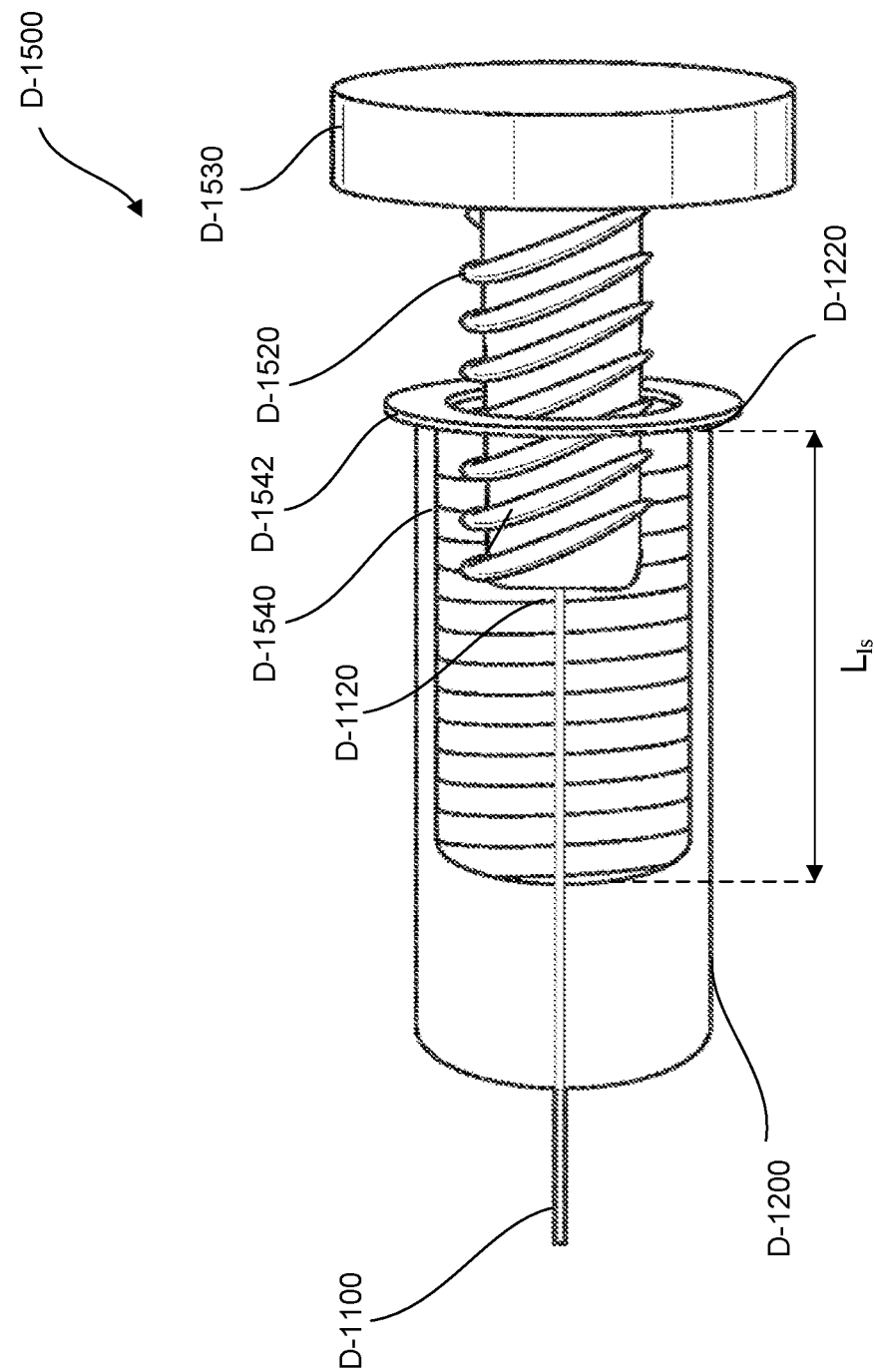
FIG. 9B is a perspective view of the adjuster in a second configuration, according to certain aspects of the disclosure.

FIGS. 9A-9B are perspective views of the adjuster D-1500 of the adjustment system in a first configuration and in a second configuration, respectively and according to certain aspects of the disclosure.

In a first configuration, the adjuster D-1500 can be a hook D-1510, as illustrated in FIG. 9A, to receive at least one finger of the operator to pull and release the filament D-1100, so as to increase and decrease the angular orientation θ of the catheter 1000 via articulation of the adjustable neck C-1000 from the extended position to the contracted position, and vice-versa.

In a second configuration, the adjuster D-1500 can include an adjuster screw D-1520 with a head surmounted by an adjuster knob D-1530 and a tip affixed to a posterior filament extremity D-1120 of the filament D-1100, and an adjuster sleeve D-1540 that receives the adjuster screw D-1520.

The adjuster sleeve D-1540 can be inserted in the secondary lumen D-1200 and be surmounted by an adjuster flange D-1542 that sits on the external extremity D-1220 of the secondary lumen D-1200. The adjuster sleeve D-1540 can have a threaded surface that extends from the external extremity D-1220 towards the main lumen B-1000 along a sleeve length $L_{sl}$, wherein the threaded surface engages into a threaded surface of the adjuster screw D-1520.

The operator can turn the adjuster knob D-1530 in a first direction, e.g. clockwise, to unscrew the adjuster screw D-1520 from the adjuster sleeve D-1540 and pulls the filament D-1100, so as to increase the angular orientation θ of the catheter 1000 via articulation of the adjustable neck C-1000 from the extended position to the contracted position.

Similarly, the operator can turn the adjuster knob D-1530 in a second direction opposite to the first direction, e.g. contra-clockwise, to screw the adjuster screw D-1520 into the adjuster sleeve D-1540 and releases the filament D-1100, so as to decrease the angular orientation θ of the catheter 1000 via articulation of the adjustable neck C-1000 from the contracted position to the extended position.

The sleeve length $L_{ls}$ can be sufficiently long to have the tensioner C-1400 of the adjustable neck C-1000 maximizing the adjustable bias force between the main lumen B-1000 and the head A-1000 when the adjustable neck C-1000 is in the contracted position and to have the tensioner C-1400 of the adjustable neck C-1000 minimizing the adjustable bias force between the main lumen B-1000 and the head A-1000 when the adjustable neck C-1000 is in the extended position.

In addition, the adjuster sleeve D-1540 and the adjuster screw D-1520 can have predetermined pitch sizes to provide a predetermined precision for the articulation of the adjustable neck C-1000 and the adjustment of the angular orientation θ of the catheter 1000. For example, the predetermined pitch sizes can be between 0.01 millimeter and 1.00 millimeter, and preferably between 0.01 millimeter and 0.50 millimeter to provide a precision between 0.001 millimeter and 1.00 millimeter, and preferably between 0.01 millimeter and 0.50 millimeter per complete rotation of the adjuster knob D-1530.

Figure 10:
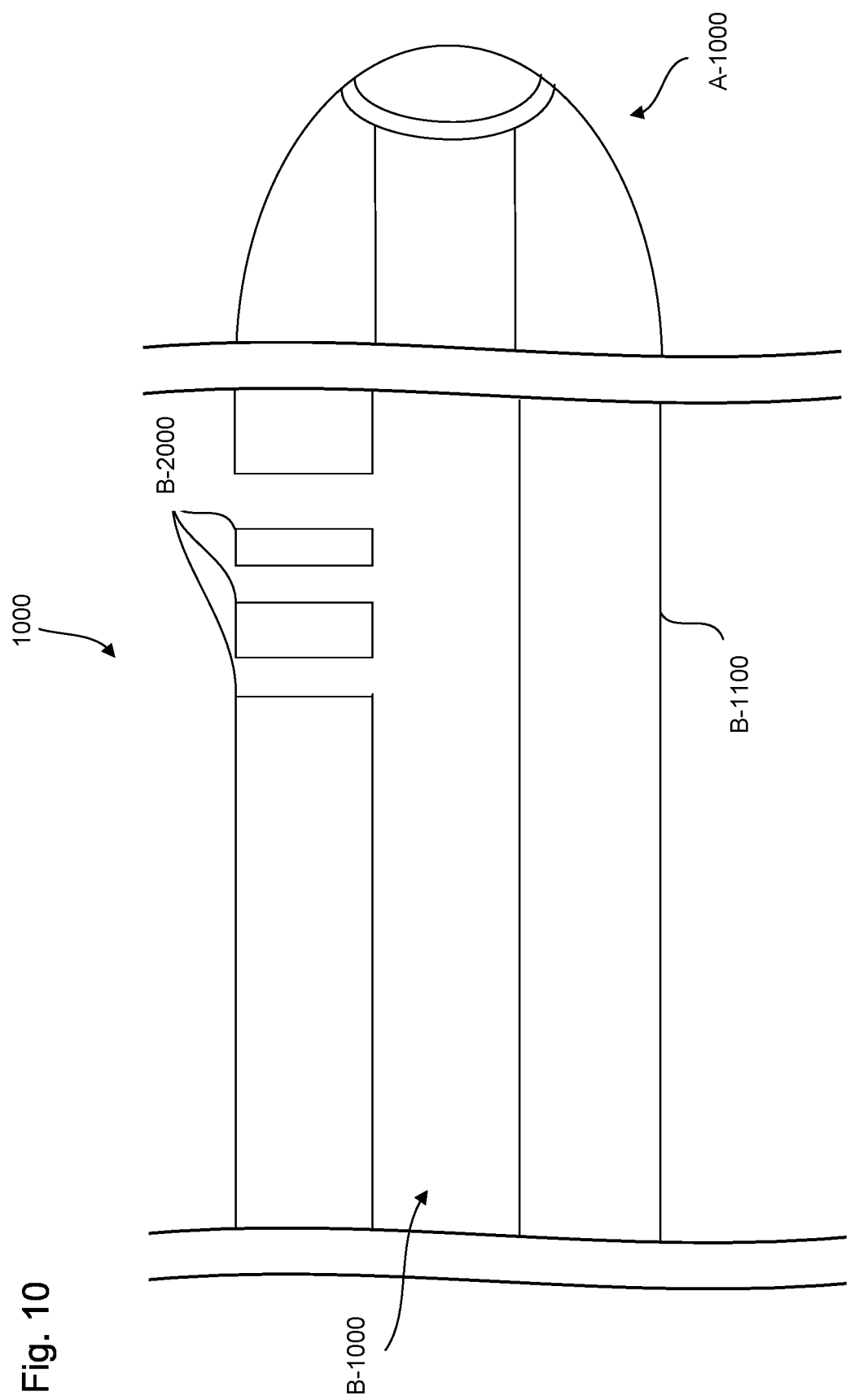
FIG. 10 is a sectional view of the catheter with lateral orifices connected to the main lumen, according to certain aspects of the disclosure.

FIG. 10 is a sectional view of the catheter 1000 with lateral orifices B-2000 connected to the main lumen B-1000, according to certain aspects of the disclosure.

In addition, the catheter 1000 can include lateral orifices B-2000 that go through the main lumen wall B-1100 to open the main lumen B-1000 on external environment. For example, the lateral orifices B-2000 can be configured to drain large body cavities such as chest wall cavity or abscess collection. Each lateral orifice of the lateral orifices B-2000 can have predetermined physical characteristics, e.g. dimensions, shapes, locations, depending on configured usages.

For example, a lateral orifice configured to drain large cavities, e.g. chest wall cavities, can have a larger diameter than a lateral orifice configured to drain small cavities, e.g. abscess cavities.

The foregoing discussion discloses and describes merely exemplary embodiments of an object of the present disclosure. As will be understood by those skilled in the art, an object of the present disclosure may be embodied in other specific forms without departing from the spirit or essential characteristics thereof. Accordingly, the present disclosure is intended to be illustrative, but not limiting of the scope of an object of the present disclosure as well as the claims.

Numerous modifications and variations on the present disclosure are possible in light of the above teachings. It is therefore to be understood that within the scope of the appended claims, the disclosure may be practiced otherwise than as specifically described herein.

What is claimed is:

1. A catheter, comprising:
   a head including:
   a head orifice, and
   a head channel connected to the head orifice;
   a primary lumen wall that defines an internal primary lumen volume;
   an adjustable neck that connects the head channel to the internal primary lumen volume, the adjustable neck including:
   an anterior neck ring affixed to the head,
   a posterior neck ring affixed to the primary lumen wall, and
   a tensioner that generates a bias force between the anterior neck ring and the posterior neck ring; and
   a secondary lumen including:
   an internal portion that is enclosed along the primary lumen wall, and
   an external portion that protrudes from the primary lumen wall,
   a filament that runs through the internal portion and the external portion, the filament including:
   an anterior filament end affixed to the anterior neck ring, and
   a posterior filament end that exits from the external portion, and
   an adjuster that pulls and releases the posterior filament end to provide a decrease and an increase, respectively, of an inter-neck ring distance between the anterior neck ring and the posterior neck ring,
   wherein the increase of the inter-neck ring distance decreases the bias force and provides an angular orientation increase of the catheter while the decrease of the inter-neck ring distance increases the bias force and provides an angular orientation decrease of the catheter, and
   wherein the posterior neck ring further includes a secondary lumen stop to block the internal portion and to let the filament freely pass through the posterior neck ring.

2. The catheter of claim 1, wherein the adjuster includes a hook to pull and release the posterior filament end.

3. The catheter of claim 1, wherein the adjuster includes a threaded adjuster sleeve, and
   an adjuster screw engaged in the threaded adjuster sleeve, the adjuster screw having
   a tip affixed to the posterior filament end, and
   an adjuster knob operable to pull and release the posterior filament end.

4. The catheter of claim 1, wherein the anterior neck ring further includes an anchor to affix the anterior filament end to the anterior neck ring.

5. The catheter of claim 4, wherein the anchor includes
   a filament hole in the anterior neck ring to receive the anterior filament end,
   a filament screw, and
   a threaded hole in the anterior neck ring that intersects the filament hole to receive the filament screw and affix the anterior filament end to the anterior neck ring.

6. The catheter of claim 1, wherein the secondary lumen stop includes
   a first hole to receive the internal portion and a second hole going through the first hole to let the filament pass therethrough.

7. A catheter, comprising:
   a head including:
   a head orifice, and
   a head channel connected to the head orifice;
   a primary lumen wall that defines an internal primary lumen volume;
   an adjustable neck that connects the head channel to the internal primary lumen volume, the adjustable neck including:
   an anterior neck ring affixed to the head,
   a posterior neck ring affixed to the primary lumen wall, and
   a tensioner that generates a bias force between the anterior neck ring and the posterior neck ring;
   an adjustment system partially enclosed in the primary lumen wall that provides a decrease and an increase, respectively, of an inter neck ring distance between the anterior neck ring and the posterior neck ring,
   wherein the decrease of the inter neck ring distance increases the bias force and provides an angular orientation increase of the catheter while the increase of the inter neck ring distance decreases the bias force and provides an angular orientation decrease of the catheter,
   wherein the tensioner includes at least one spring extending between the anterior neck ring and the posterior neck ring, and
   wherein the tensioner includes an anti-buckling system to prevent the at least one spring from buckling.

8. The catheter of claim 7, wherein the anti-buckling system includes
   a posterior seat that provides support between the posterior neck ring and a posterior spring of the at least one spring,
   an anterior seat that provides support between the anterior neck ring and an anterior spring of the at least one spring, and
   one separator that provides support between the posterior spring and the anterior spring.

9. The catheter of claim 8, wherein the separator includes
   a separator base portion, and
   a separator flange portion that protrudes substantially perpendicular from the separator base portion to hold an anterior side of the anterior spring and a posterior side of the posterior spring.

10. The catheter of claim 8, wherein the anterior seat includes
    an anterior seat base portion, and
    an anterior seat flange portion that protrudes substantially perpendicular from the anterior seat base portion to hold an anterior side of the anterior spring.

11. The catheter of claim 8, wherein the posterior seat includes
    a posterior seat base portion, and
    a posterior seat flange portion that protrudes substantially perpendicular from the posterior seat base portion to hold a posterior side of the posterior spring.

12. The catheter of claim 7, wherein the tensioner is positioned inside a neck tube of the adjustable neck.

13. The catheter of claim 12, wherein the adjustable neck tube includes a plurality of bulges placed along a length of the neck tube to facilitate the increase and the decrease of the inter neck ring distance.

\* \* \* \* \*